US011229735B1

(12) United States Patent
Alves

(10) Patent No.: US 11,229,735 B1
(45) Date of Patent: Jan. 25, 2022

(54) IV POLE CLAMP

(71) Applicant: Miguel Alves, W. Warwick, RI (US)

(72) Inventor: Miguel Alves, W. Warwick, RI (US)

( * ) Notice: Subject to any disclaimer, the term of this patent is extended or adjusted under 35 U.S.C. 154(b) by 65 days.

(21) Appl. No.: 16/807,234

(22) Filed: Mar. 3, 2020

(51) Int. Cl.
*A61M 5/14* (2006.01)
*F16M 13/02* (2006.01)

(52) U.S. Cl.
CPC ........ *A61M 5/1418* (2013.01); *A61M 5/1415* (2013.01); *F16M 13/02* (2013.01); *F16M 13/022* (2013.01); *A61M 2209/082* (2013.01)

(58) Field of Classification Search
CPC . F16M 13/022; A61G 7/0503; A61M 5/1415; A61M 5/1414; A61M 2209/082
See application file for complete search history.

(56) References Cited

U.S. PATENT DOCUMENTS

| 1,865,757 | A | * | 7/1932 | Honsowetz | ............ | A47C 21/00 211/172 |
| 4,262,872 | A | * | 4/1981 | Kodet | ...................... | A61G 1/04 248/291.1 |
| 4,511,158 | A | | 4/1985 | Varga | | |
| 4,840,391 | A | * | 6/1989 | Schneider | ................ | A61G 5/10 248/121 |
| 4,969,768 | A | * | 11/1990 | Young | ...................... | A61G 5/10 403/24 |
| 5,083,807 | A | * | 1/1992 | Bobb | ....................... | A61G 5/10 248/231.51 |
| 5,174,533 | A | * | 12/1992 | Pryor | ................... | A61M 5/1415 248/231.71 |
| 5,236,213 | A | | 8/1993 | Trickett | | |
| 5,355,539 | A | | 10/1994 | Boettger | | |
| 5,358,205 | A | | 10/1994 | Starkey | | |
| 5,421,548 | A | * | 6/1995 | Bennett | ..................... | A61G 5/10 248/129 |
| 5,482,239 | A | | 1/1996 | Smith | | |
| 5,699,988 | A | * | 12/1997 | Boettger | ................... | A61G 5/10 248/122.1 |
| 5,836,327 | A | * | 11/1998 | Davis | ..................... | A45B 11/00 135/16 |
| 6,179,260 | B1 | | 1/2001 | Ohanian | | |
| 9,700,666 | B2 | | 7/2017 | Rowston | | |
| 10,272,005 | B2 | | 4/2019 | Bongard | | |
| 2010/0180408 | A1 | | 7/2010 | Denning | | |

(Continued)

FOREIGN PATENT DOCUMENTS

CA          2149336          1/1993

*Primary Examiner* — Bradley Duckworth
(74) *Attorney, Agent, or Firm* — Kyle A. Fletcher, Esq.

(57) ABSTRACT

The IV pole clamp is a mechanical structure. The IV pole clamp is configured for use with an IV pole. The IV pole is a prism-shaped post structure used to elevate an IV bag. The IV bag is elevated such that a pharmacologically active media can be gravity fed into the patient. The IV pole clamp attaches the IV pole to a mounting surface such as a counter. The IV pole clamp is a rotating structure such that the cant between the center axis of the IV pole and the force of gravity is adjustable. The IV pole clamp comprises a pedestal structure, a stanchion, and a clamp structure. The pedestal structure and the clamp structure attach to the stanchion. The pedestal structure attaches the stanchion to the mounting surface. The clamp structure attaches the IV pole to the stanchion.

18 Claims, 5 Drawing Sheets

(56) References Cited

U.S. PATENT DOCUMENTS

2011/0121149 A1* 5/2011 Herskovic ............ A61G 7/0503
                                                    248/223.41
2020/0352806 A1* 11/2020 Fischer ................ A61G 13/101
2021/0146038 A1* 5/2021 Johnson .............. A61M 5/1415

* cited by examiner

IV POLE CLAMP

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical and veterinary science including devices and accessories for bringing media into a body, more specifically, a stand for supporting infusion devices. (A61M5/1415)

SUMMARY OF INVENTION

The IV pole clamp is a mechanical structure. The IV pole clamp is configured for use with an IV pole. The IV pole is a prism-shaped post structure used to elevate an IV bag. The IV bag contains a pharmacologically active media that is introduced intravenously into a patient for therapeutic purposes. The IV bag is elevated such that the pharmacologically active media can be gravity fed into the patient. The IV pole clamp attaches the IV pole to a mounting surface such as a counter. The IV pole clamp is a rotating structure such that the cant between the center axis of the IV pole and the force of gravity is adjustable. The IV pole clamp comprises a pedestal structure, a stanchion, and a clamp structure. The pedestal structure and the clamp structure attach to the stanchion. The pedestal structure attaches the stanchion to the mounting surface. The clamp structure attaches the IV pole to the stanchion.

These together with additional objects, features and advantages of the IV pole clamp will be readily apparent to those of ordinary skill in the art upon reading the following detailed description of the presently preferred, but nonetheless illustrative, embodiments when taken in conjunction with the accompanying drawings.

In this respect, before explaining the current embodiments of the IV pole clamp in detail, it is to be understood that the IV pole clamp is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the IV pole clamp.

It is therefore important that the claims be regarded as including such equivalent construction insofar as they do not depart from the spirit and scope of the IV pole clamp. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
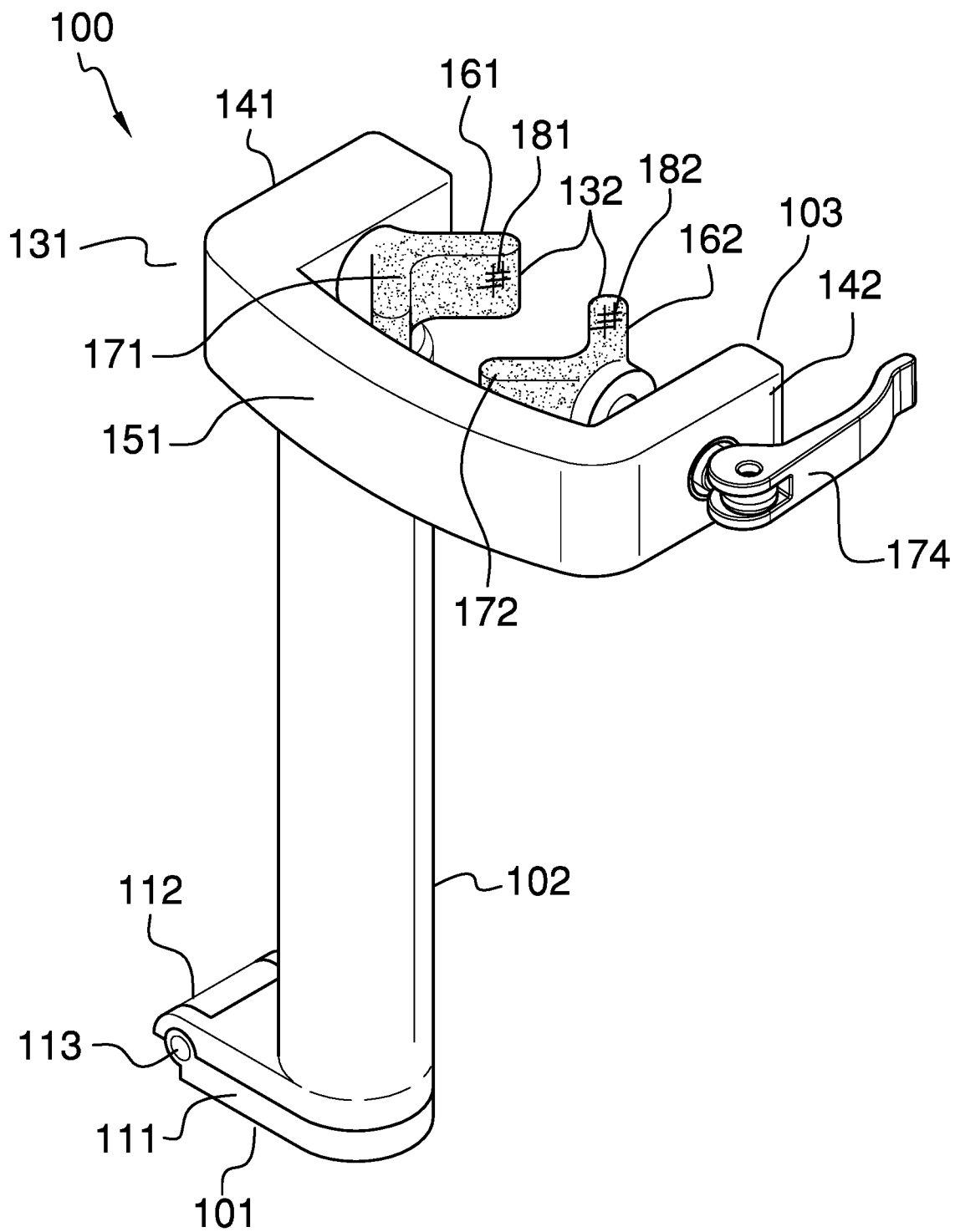
FIG. 1 is a perspective view of an embodiment of the disclosure.
Figure 2:
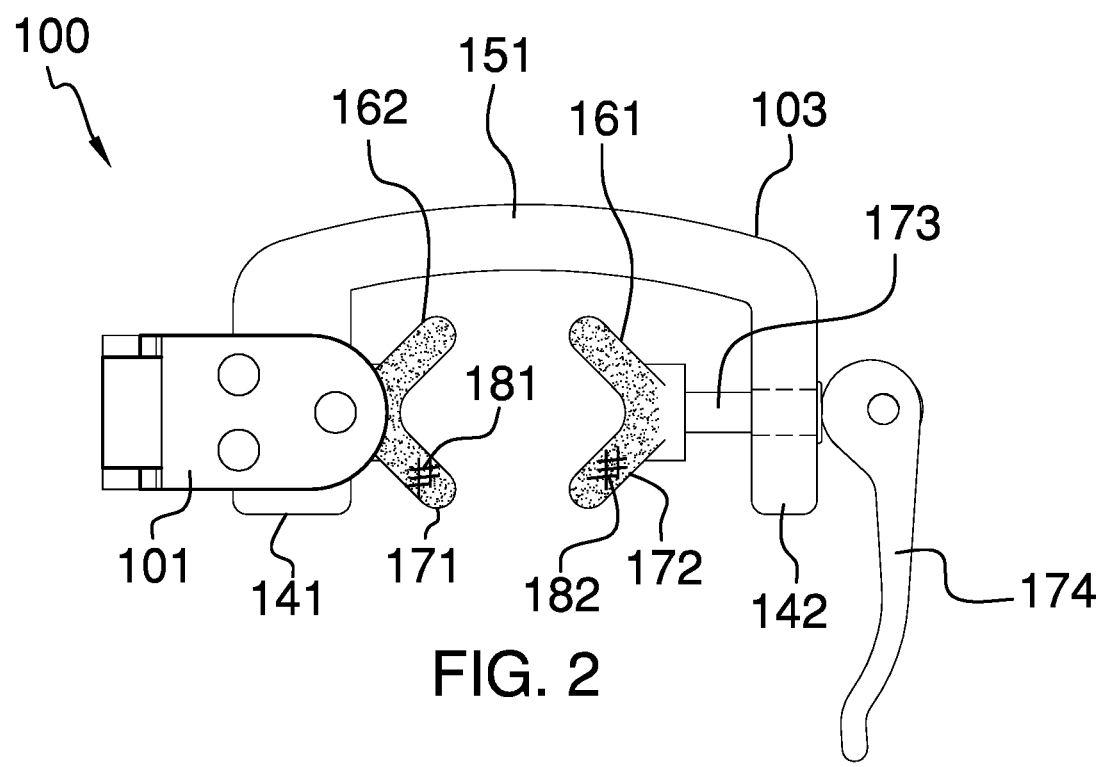
FIG. 2 is a bottom view of an embodiment of the disclosure.
Figure 3:
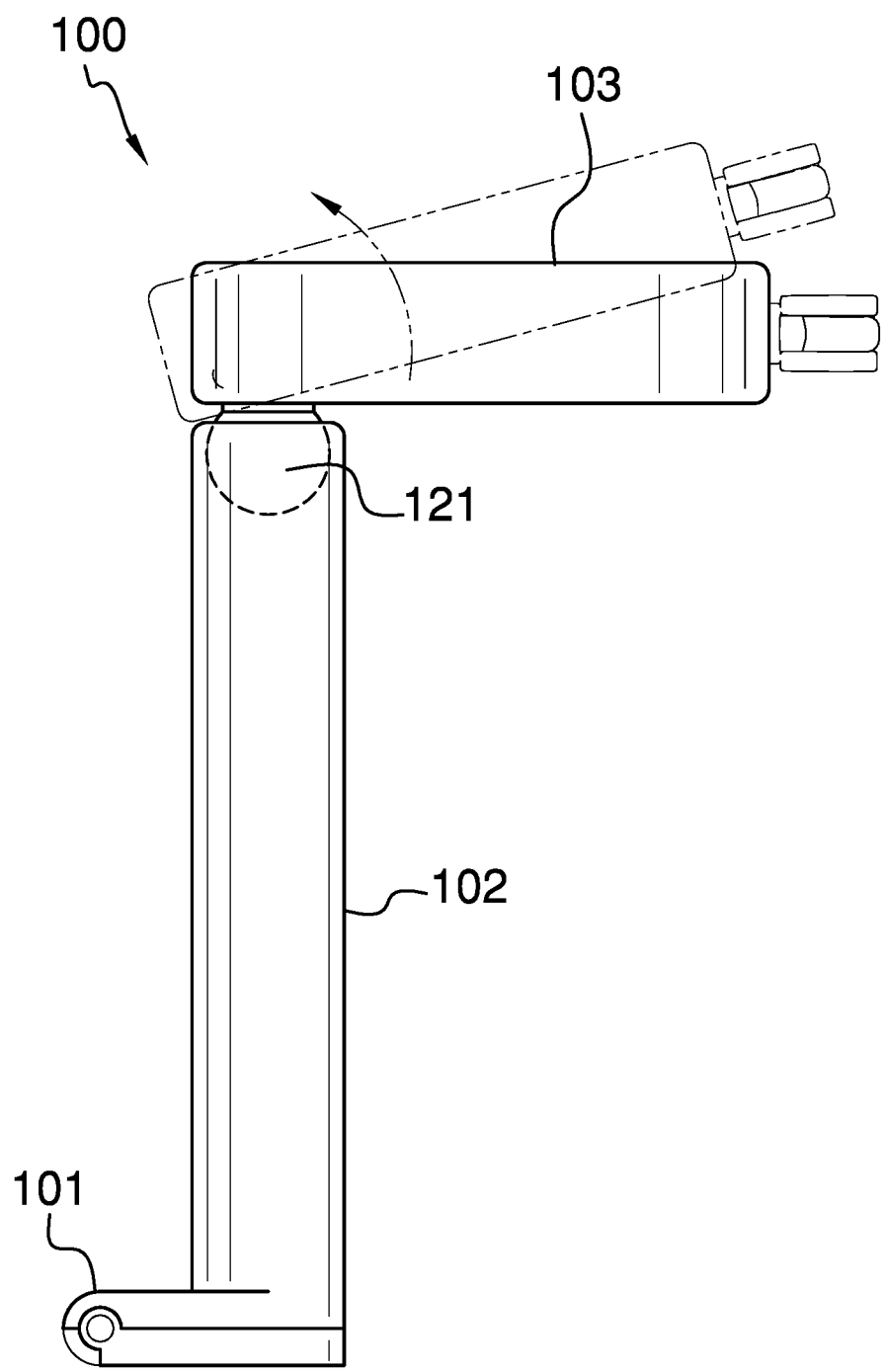
FIG. 3 is a side view of an embodiment of the disclosure.
Figure 4:
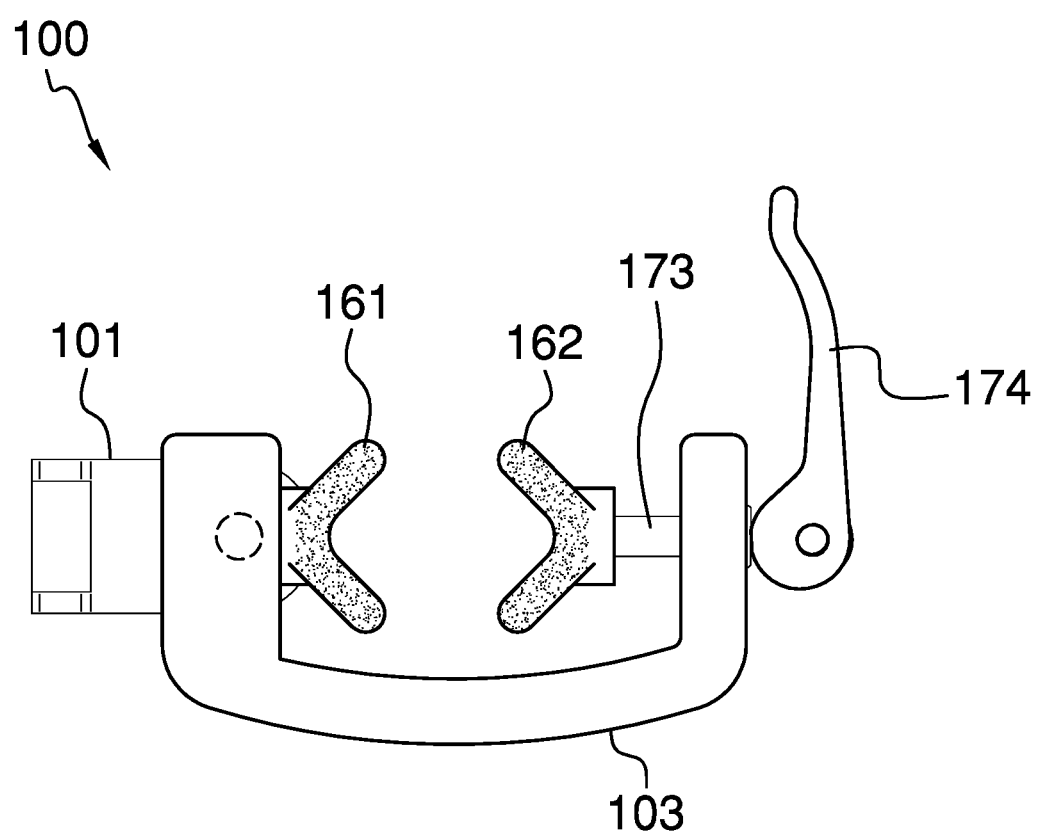
FIG. 4 is a top view of an embodiment of the disclosure.
Figure 5:
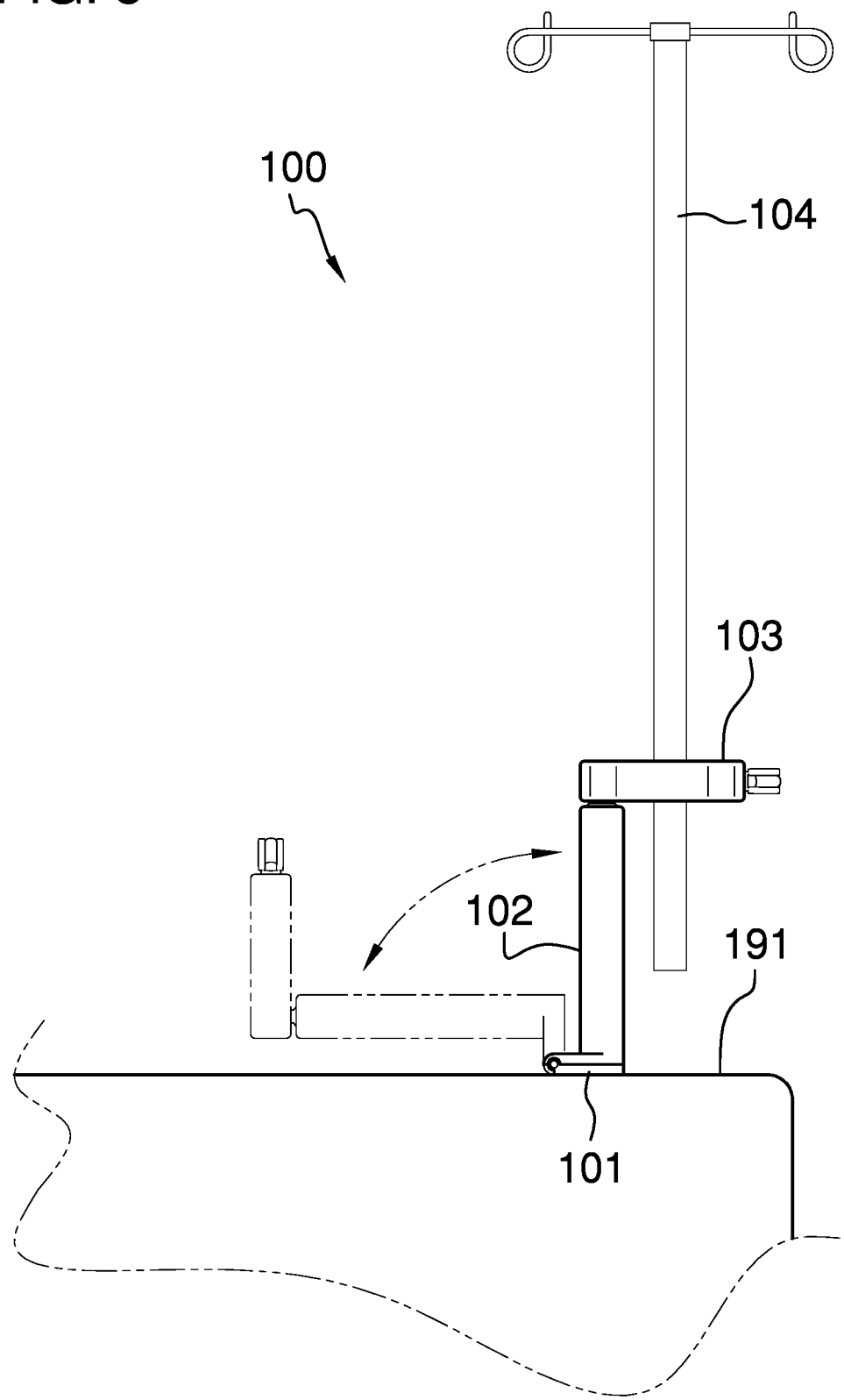
FIG. 5 is an in-use view of an embodiment of the disclosure.

Detailed reference will now be made to one or more potential embodiments of the disclosure, which are illustrated in FIGS. 1 through 5.

The IV pole clamp 100 (hereinafter invention) is a mechanical structure. The invention 100 is configured for use with an IV pole 104. The IV pole 104 is a prism-shaped post structure used to elevate an IV bag. The IV bag contains a pharmacologically active media that is introduced intravenously into a patient for therapeutic purposes. The IV bag is elevated such that the pharmacologically active media can be gravity fed into the patient. The invention 100 attaches the IV pole 104 to a mounting surface 191 such as a counter. The invention 100 is a rotating structure such that the cant between the center axis of the IV pole 104 and the force of gravity is adjustable. The invention 100 comprises a pedestal structure 101, a stanchion 102, and a clamp structure 103. The pedestal structure 101 and the clamp structure 103 attach to the stanchion 102. The pedestal structure 101 attaches the stanchion 102 to the mounting surface 191. The clamp structure 103 attaches the IV pole 104 to the stanchion 102.

The pedestal structure 101 is a mechanical structure. The pedestal structure 101 attaches the stanchion 102 to the mounting surface 191 such that the stanchion 102 rotates relative to the mounting surface 191. The pedestal structure 101 transfers the load of the stanchion 102, the clamp structure 103, and the IV pole 104 to the mounting surface 191. The pedestal structure 101 is a rotating structure such that the cant of the stanchion 102 relative to the perpendicular of the mounting surface 191 is adjustable. The pedestal structure 101 comprises a base pedestal 111, a rotating pedestal 112, and a locking pedestal hinge 113.

The base pedestal 111 is a prism-shaped structure. The base pedestal 111 is a disk-shaped structure. The base pedestal 111 attaches directly to the mounting surface 191. The rotating pedestal 112 is a prism-shaped structure. The rotating pedestal 112 is a disk-shaped structure. The rotating pedestal 112 attaches to the mounting surface 191 such that the rotating pedestal 112 rotates relative to the base pedestal 111.

The locking pedestal hinge 113 is a fastening structure commonly referred to as a locking hinge. The locking pedestal hinge 113 attaches the rotating pedestal 112 to the base pedestal 111 such that the position of the rotating pedestal 112 rotates relative to the base pedestal 111. The locking pedestal hinge 113 fixes the position of the rotating pedestal 112 relative to the base pedestal 111 such that the cant between the center axis of the stanchion 102 and the force of gravity is adjustable.

The locking pedestal hinge 113 attaches the rotating pedestal 112 to the base pedestal 111 such that a congruent end of the disk structure of the rotating pedestal 112 rotates from a position flush to a congruent end of the disk structure of the base pedestal 111 to a position where a cant is formed between the proximal congruent faces of rotating pedestal 112 and the base pedestal 111.

The stanchion 102 is a prism-shaped structure. The stanchion 102 is an extension structure. The pedestal structure 101 attaches to the inferior congruent end of the prism structure of the stanchion 102. The clamp structure 103 attaches to the superior congruent end of the prism structure of the stanchion 102. The superior congruent end of the prism structure of the stanchion 102 is distal from the inferior congruent end of the prism structure of the stanchion 102. The stanchion 102 extends the reach between the pedestal structure 101 and the clamp structure 103. The stanchion 102 further comprises a locking stanchion 102 hinge 121.

The locking stanchion 102 hinge 121 is a fastening structure referred to as a locking hinge. The locking stanchion 102 hinge 121 attaches the clamp structure 103 to the superior congruent end of the stanchion 102 such that the position of the clamp structure 103 rotates relative to the superior congruent end of the stanchion 102. The locking stanchion 102 hinge 121 fixes the position of the clamp structure 103 relative to the superior congruent end of the stanchion 102 such that the cant between the clamp structure 103 and the center axis of the stanchion 102 is adjustable.

The locking stanchion 102 hinge 121 attaches the clamp structure 103 to the stanchion 102 such that the plane formed by the center axes of the first arm 141 and the second arm 142 of the clamp structure 103 rotates relative to the center axis of the prism structure of the stanchion 102.

The clamp structure 103 is a mechanical structure. The clamp structure 103 physically attaches the IV pole 104 to the invention 100. The clamp structure 103 is a hyoid shaped structure. The clamp structure 103 grips the IV pole 104 within the concave surface formed by the hyoid shape of the clamp structure 103. The clamp structure 103 comprises a hyoid structure 131 and a plurality of grips 132.

The hyoid structure 131 is a U-shaped structure. The term hyoid is defined elsewhere in this disclosure. The hyoid structure 131 forms a semi-enclosed space. The hyoid structure 131 is sized such that an IV pole 104 can fit into the concave surface formed by the hyoid structure 131 between the first arm 141 and the second arm 142 of the U-shape of the hyoid structure 131. The hyoid structure 131 comprises a first arm 141, a second arm 142, and a first crossbeam 151.

The first arm 141 is the first arm 141 of the characteristic hyoid shape of the hyoid structure 131. The second arm 142 is the second arm 142 of the characteristic hyoid shape of the hyoid structure 131. The first crossbeam 151 is the crossbeam of the characteristic hyoid shape of the hyoid structure 131. The first crossbeam 151 attaches the first arm 141 to the second arm 142 such that the first arm 141 and the second arm 142 project away from the first crossbeam 151 in the same direction.

Each of the plurality of grips 132 is a U-shaped structure. Each of the plurality of grips 132 attaches to an arm selected from the group consisting of the first arm 141 and the second arm 142 of the U-shape of the hyoid structure 131. The IV pole 104 is positioned between the plurality of grips 132. The span of the distance between the plurality of grips 132 is adjustable such that the plurality of grips 132 can be tightened around the IV pole 104 to secure the IV pole 104 to the invention 100. The plurality of grips 132 comprises a first grip 161 and a second grip 162.

The first grip 161 is a grip selected from the plurality of grips 132. The first grip 161 attaches to the first arm 141 of the hyoid structure 131 such that the first grip 161 mounts in the concave surface formed by the hyoid structure 131. The first grip 161 comprises a first U-shaped structure 171 and a first elastic cover 181.

The first elastic cover 181 is an elastic polyurethane coating that is applied to the exterior surfaces of the first grip 161. The first elastic cover 181 protects the IV pole 104 from damage by the first grip 161.

The first U-shaped structure 171 is a U-shaped structure. The U-shaped structure is defined elsewhere in this disclosure. The first U-shaped structure 171 is sized such that the first arm of the U-Shape of the first U-shaped structure 171 and the second arm of the U-shape of the first U-shaped structure 171 fit around the lateral face of the IV pole 104. The crossbeam of the first U-shaped structure 171 attaches to the first arm 141 such that the first U-shaped structure 171 maintains a fixed position relative to the first arm 141.

The second grip 162 is a grip selected from the plurality of grips 132. The second grip 162 attaches to the second arm of the hyoid structure 131 such that the second grip 162 mounts in the concave surface formed by the hyoid structure 131. The IV pole 104 attaches to the invention 100 by securing the IV pole 104 between the first grip 161 and the second grip 162.

The second grip 162 comprises a second U-shaped structure and a second elastic cover 182. The second grip 162 further comprises a binder bolt 173, and adjustment arm 174.

The second elastic cover 182 is an elastic polyurethane coating that is applied to the exterior surfaces of the second grip 162. The second elastic cover 182 protects the IV pole 104 from damage by the second grip 162.

The second U-shaped structure 172 is a U-shaped structure. The U-shaped structure is defined elsewhere in this disclosure. The second U-shaped structure 172 is sized such that the first arm of the U-Shape of the second U-shaped structure 172 and the second arm of the U-shape of the second U-shaped structure 172 fit around the lateral face of the IV pole 104. The second U-shaped structure 172 attaches to the second arm 142 such that the position of the second U-shaped structure 172 relative to the second arm 142 is variable. The second U-shaped structure 172 attaches to the second arm 142 such that the position of the second U-shaped structure 172 relative to the first U-shaped structure 171 is variable.

The binder bolt 173 is a prism-shaped structure that attaches the second U-shaped structure 172 to the second arm 142 of the hyoid structure 131. The binder bolt 173 is defined elsewhere in this disclosure. The crossbeam of the second U-shaped structure 172 attaches to a congruent end of the prism structure of the binder bolt 173. The binder bolt 173 has external threading (not shown), and screws into the second U-shaped structure 172.

The binder bolt 173 pivots with respect to the adjustment arm 174 in order to rotate the binder bolt with respect to the second U-shaped structure 172. The adjustment arm 174 and the binder bolt 173 are well known in the art of bicycle seat adjustment mechanisms. The span of the distance between the second grip 162 and the first grip 161 is adjusted by screwing the binder bolt 173 into or out of the second U-shaped structure 172. The pressure applied to the IV pole 104 is adjusted by adjusting the span of the distance between the first grip 161 and the second grip 162.

The following definitions were used in this disclosure:

Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Cant: As used in this disclosure, a cant is an angular deviation from one or more reference lines (or planes) such as a vertical line (or plane) or a horizontal line (or plane).

Carbamate: As used in this disclosure, a carbamate is a functional group consisting of an O—(C=O)—N structure. Carbamate is informally referred to as urethane.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Coating: As used in this disclosure, a coating refers to a substance that is applied to the exterior surface of an object such that the coating forms a new exterior surface of the object. A coating is commonly said to be formed as a layer. Paint is an example of a common coating material.

Concave: As used in this disclosure, concave is used to describe: 1) a surface that resembles the interior surface of a sphere; or, 2) a function with a curvature structure wherein a chord that connects any two points of the function will be lesser than (graphically below) or equal to the value of the function at any point along the chord.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Convex: As used in this disclosure, convex is used to describe: 1) a surface that resembles the outer surface of a sphere; or, 2) a function with a curvature structure wherein a chord that connects any two points of the function will be greater than (graphically above) or equal to the value of the function at any point along the chord.

Copolymer: As used in this disclosure, a copolymer is a polymer formed from two or more repeating molecules (also referred to as monomers).

Correspond: As used in this disclosure, the term correspond is used as a comparison between two or more objects wherein one or more properties shared by the two or more objects match, agree, or align within acceptable manufacturing tolerances.

Counter: As used in this disclosure, a counter is a horizontal surface a working space for a project. A counter is further defined with an inferior surface and a superior surface.

Cushion: As used in this disclosure a cushion is a structure formed with a pad that is used to prevent injury or damage to a person or object.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elevation: As used in this disclosure, elevation refers to the span of the distance in the superior direction between a specified horizontal surface and a reference horizontal surface. Unless the context of the disclosure suggest otherwise, the specified horizontal surface is the supporting surface the potential embodiment of the disclosure rests on. The infinitive form of elevation is to elevate.

Extension Structure: As used in this disclosure, an extension structure is an inert physical structure that is used to extend or bridge the reach between any two objects.

Exterior Screw Thread: An exterior screw thread is a ridge wrapped around the outer surface of a tube in the form of a helical structure that is used to convert rotational movement into linear movement.

Force of Gravity: As used in this disclosure, the force of gravity refers to a vector that indicates the direction of the pull of gravity on an object at or near the surface of the earth.

Form Factor: As used in this disclosure, the term form factor refers to the size and shape of an object.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Helix: As used in this disclosure, a helix is the three-dimensional structure that would be formed by a wire that is wound uniformly around the surface of a cylinder or a cone. If the wire is wrapped around a cylinder the helix is called a cylindrical helix. If the wire is wrapped around a cone, the helix is called a conical helix. A synonym for conical helix would be a volute.

Hinge: As used in this disclosure, a hinge is a device that permits the turning, rotating, or pivoting of a first object relative to a second object. A hinge designed to be fixed into a set position after rotation is called a locking hinge.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Hyoid: As used in this disclosure, a hyoid refers to a three-sided structure comprising a crossbeam, a first arm, and a second arm. In a hyoid, the first arm and the second arm project away from the crossbeam: 1) in the same direction; 2) at a roughly perpendicular angle to the crossbeam, and, 3) the span of the length of the first arm roughly equals the span of the length of the second arm. Hyoids generally have a U shaped appearance.

Inferior: As used in this disclosure, the term inferior refers to a directional reference that is parallel to and in the same direction as the force of gravity when an object is positioned or used normally.

Interior Screw Thread: An interior screw thread is a groove that is formed around the inner surface of a tube in the form of a helical structure that is used to convert rotational movement into linear movement.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Monomer: As used in this disclosure, a monomer refers to a molecular structure that bonds to itself in a repeating manner to form a polymer.

Negative Space: As used in this disclosure, negative space is a method of defining an object through the use of open or empty space as the definition of the object itself, or, through the use of open or empty space to describe the boundaries of an object.

Non-Skid Material: As used in this disclosure, a non-skid material is a material or structure that can be applied to an object such that the object is inhibited from sliding along the surface upon which the object is resting. Non-skid materials are often, but not always, adhesive, elastic, or abrasive materials.

Adjustment arm: As used in this disclosure, a adjustment arm is a first object that is formed with a cylindrical negative space that further comprises an interior screw thread such that a second object with a matching exterior screw thread can screwed into the first object forming a threaded connection. A adjustment arm is further defined with an inner diameter.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Pedestal: As used in this disclosure, a pedestal is an intermediary load bearing structure that forms a load path between a supporting surface and an object, structure, or load.

Perimeter: As used in this disclosure, a perimeter is one or more curved or straight lines that bounds an enclosed area on a plane or surface. The perimeter of a circle is commonly referred to as a circumference.

Pharmacologically Active Media: As used in this disclosure, a pharmacologically active media refers to a chemical substance that has a biochemical or physiological effect on a biological organism.

Plate: As used in this disclosure, a plate is a shallow concave crockery item. The superior surface of the plate presents a concave surface. The concave surface contains fluids associated with a foodstuff. By shallow is meant that the span of the vertical depth from the apex of the concave surface to the superior edge of the concave surface is such that foodstuffs contained in the plate can be cut from a horizontal angle of attack.

Polymer: As used in this disclosure, a polymer refers to a molecular chain that comprises multiple repeating units known as monomers. The repeating unit may be an atom or a molecular structure.

Polyurethane: As used in this disclosure, a polyurethane is a copolymer wherein the one or more monomer chains are linked together carbamates.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Reach: As used in this disclosure, reach refers to a span of distance between any two objects.

Relaxed Shape: As used in this disclosure, a structure is considered to be in its relaxed state when no shear, strain, or torsional forces are being applied to the structure.

Screw: As used in this disclosure, to screw is a verb meaning: 1) to fasten or unfasten (unscrew) a threaded connection; or 2) to attach a helical structure to a solid structure.

Stanchion: As used in this disclosure, a stanchion refers to a vertically oriented prism-shaped pole, post, or support.

Superior: As used in this disclosure, the term superior refers to a directional reference that is parallel to and in the opposite direction of the force of gravity when an object is positioned or used normally.

Suspend: As used in this disclosure, to suspend an object means to support an object such that the inferior end of the object does not form a significant portion of the load path of the object. Include inferior superior and load path.

Therapeutic: As used in this disclosure, therapeutic is an adjective that refers to a medical, ameliorative, or hygienic substance, process, or procedure.

Threaded Connection: As used in this disclosure, a threaded connection is a type of fastener that is used to join a first cylindrical object and a second cylindrical object together. The first cylindrical object is fitted with a first fitting selected from an interior screw thread or an exterior screw thread. The second cylindrical object is fitted with the remaining screw thread. The cylindrical object fitted with the exterior screw thread is placed into the remaining cylindrical object such that: 1) the interior screw thread and the exterior screw thread interconnect; and, 2) when the cylindrical object fitted with the exterior screw thread is rotated the rotational motion is converted into linear motion that moves the cylindrical object fitted with the exterior screw thread either into or out of the remaining cylindrical object. The direction of linear motion is determined by the direction of rotation.

U-Shaped Structure: As used in this disclosure, a U-shaped structure refers to a three-sided structure comprising a crossbeam, a first arm, and a second arm. In a U-shaped structure, the first arm and the second arm are prism-shaped structures that project away from the crossbeam: 1) in the same direction; 2) at a roughly perpendicular angle to the crossbeam, and, 3) the span of the length of the first arm roughly equals the span of the length of the second arm.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An IV pole clamp comprising
a pedestal structure, a stanchion, and a clamp structure;
wherein the pedestal structure and the clamp structure attach to the stanchion;
wherein the IV pole clamp is a mechanical structure;
wherein the IV pole clamp is configured for use with an IV pole;
wherein the IV pole is a prism-shaped structure;
wherein the IV pole clamp attaches the IV pole to a mounting surface;
wherein the IV pole clamp is a rotating structure such that the cant between the center axis of the IV pole and the force of gravity is adjustable;
wherein the pedestal structure comprises a base pedestal, a rotating pedestal, and a locking pedestal hinge;
wherein the locking pedestal hinge attaches the rotating pedestal to the base pedestal such that the position of the rotating pedestal rotates relative to the base pedestal;
wherein the base pedestal is a prism-shaped structure;
wherein the base pedestal is a disk-shaped structure;
wherein the base pedestal attaches directly to the mounting surface.

2. The IV pole clamp according to claim 1
wherein the pedestal structure is a mechanical structure;
wherein the pedestal structure attaches the stanchion to the mounting surface;
wherein the pedestal structure transfers the load of the stanchion, the clamp structure, and the IV pole to the mounting surface;
wherein the pedestal structure is a rotating structure such that the cant of the stanchion relative to the perpendicular of the mounting surface is adjustable.

3. The IV pole clamp according to claim 2
wherein the stanchion is a prism-shaped structure;
wherein the stanchion is an extension structure;
wherein the stanchion further comprises an inferior congruent end and a superior congruent end;
wherein the superior congruent end of the prism-shaped structure of the stanchion is distal from the inferior congruent end of the prism-shaped structure of the stanchion;
wherein the pedestal structure attaches to the inferior congruent end of the prism-shaped structure of the stanchion;
wherein the clamp structure attaches to the superior congruent end of the prism-shaped structure of the stanchion;
wherein the stanchion extends between the pedestal structure and the clamp structure.

4. The IV pole clamp according to claim 3
wherein the clamp structure is a mechanical structure;
wherein the clamp structure physically attaches the IV pole to the IV pole clamp.

5. The IV pole clamp according to claim 4
wherein the stanchion further comprises a locking stanchion hinge;
wherein the locking stanchion hinge is a locking hinge;
wherein the locking stanchion hinge attaches the clamp structure to the superior congruent end of the stanchion such that the position of the clamp structure rotates relative to the superior congruent end of the stanchion;
wherein the locking stanchion hinge fixes the position of the clamp structure relative to the superior congruent end of the stanchion such that the cant between the clamp structure and the center axis of the stanchion is adjustable.

6. The IV pole clamp according to claim 5
wherein the clamp structure comprises a hyoid structure and a plurality of grips;
wherein the plurality of grips attach to the hyoid structure.

7. The IV pole clamp according to claim 6
wherein the rotating pedestal is a prism-shaped structure;
wherein the rotating pedestal is a disk-shaped structure;
wherein the rotating pedestal attaches to the mounting surface such that the rotating pedestal rotates relative to the base pedestal.

8. The IV pole clamp according to claim 7
wherein the locking pedestal hinge is a locking hinge;
wherein the locking pedestal hinge attaches the rotating pedestal to the base pedestal such that the position of the rotating pedestal rotates relative to the base pedestal;
wherein the locking pedestal hinge fixes the position of the rotating pedestal relative to the base pedestal such that the cant between the center axis of the stanchion and the force of gravity is adjustable.

9. The IV pole clamp according to claim 8 wherein the locking pedestal hinge attaches the rotating pedestal to the base pedestal such that a congruent end of the disk-shaped structure of the rotating pedestal rotates from a position flush to a congruent end of the disk structure of the base pedestal to a position where a cant is formed between the proximal congruent faces of rotating pedestal and the base pedestal.

10. The IV pole clamp according to claim 9 wherein the locking stanchion hinge attaches the clamp structure to the stanchion such that the plane formed by the center axes of a first arm and a second arm of the clamp structure rotates relative to the center axis of the prism-shaped structure of the stanchion.

11. The IV pole clamp according to claim 10
wherein the hyoid structure is a U-shaped structure;
wherein the hyoid structure forms a semi-enclosed space;
wherein the hyoid structure is sized such that an IV pole can fit into the concave surface formed by the hyoid structure between a first arm and a second arm of the U-shape of the hyoid structure.

12. The IV pole clamp according to claim 11
wherein the hyoid structure comprises the first arm, the second arm, and a first crossbeam;
wherein the first crossbeam attaches the first arm to the second arm such that the first arm and the second arm project away from the first crossbeam in the same direction.

13. The IV pole clamp according to claim 12
wherein each of the plurality of grips is a U-shaped structure;
wherein each of the plurality of grips attaches to an arm selected from the group consisting of the first arm and the second arm of the U-shape of the hyoid structure;
wherein the IV pole is positioned between the plurality of grips;
wherein the span of the distance between the plurality of grips is adjustable such that the plurality of grips can be tightened around the IV pole to secure the IV pole to the IV pole clamp.

14. The IV pole clamp according to claim 13
wherein the plurality of grips comprises a first grip and a second grip;
wherein the first grip is a grip selected from the plurality of grips;
wherein the first grip attaches to the first arm of the hyoid structure such that the first grip mounts in the concave surface formed by the hyoid structure;
wherein the second grip is a grip selected from the plurality of grips;
wherein the second grip attaches to the second arm of the hyoid structure such that the second grip mounts in the concave surface formed by the hyoid structure;
wherein the IV pole attaches to the IV pole clamp by securing the IV pole between the first grip and the second grip.

15. The IV pole clamp according to claim 14
wherein the first grip comprises a first U-shaped structure and a first elastic cover;
wherein the first elastic cover is an elastic polyurethane coating that is applied to the exterior surfaces of the first grip;
wherein the second grip comprises a second U-shaped structure and a second elastic cover;
wherein the second elastic cover is an elastic polyurethane coating that is applied to the exterior surfaces of the second grip.

16. The IV pole clamp according to claim 15
wherein the first U-shaped structure is sized such that the first arm of the U-shape of the first U-shaped structure and the second arm of the U-shape of the first U-shaped structure fit around the lateral face of the IV pole;
wherein a crossbeam of the first U-shaped structure attaches to the first arm such that the first U-shaped structure maintains a fixed position relative to the first arm.

17. The IV pole clamp according to claim 16
wherein the second U-shaped structure is sized such that the first arm of the U-shape of the second U-shaped structure and the second arm of the U-shape of the second U-shaped structure fit around the lateral face of the IV pole;
wherein the second U-shaped structure attaches to the second arm such that the position of the second U-shaped structure relative to the second arm is variable;
wherein the second U-shaped structure attaches to the second arm such that the position of the second U-shaped structure relative to the first U-shaped structure is variable.

18. The IV pole clamp according to claim 17
wherein the second grip further comprises a binder bolt and an adjustment arm;
wherein the binder bolt is a prism-shaped structure that attaches the second U-shaped structure to the second arm of the hyoid structure;
wherein the crossbeam of the second U-shaped structure attaches to a congruent end of the prism structure of the binder bolt;
wherein the binder bolt pivots with respect to the adjustment arm in order to rotate the binder bolt into or out of the second U-shaped structure to the second arm;
wherein the span of the distance between the second grip and the first grip is adjusted by screwing the binder bolt into or out of the second U-shaped structure;
wherein the pressure applied to the IV pole is adjusted by adjusting the span of the distance between the first grip and the second grip.

* * * * *